United States Patent [19]
Novello

[11] 3,969,518
[45] July 13, 1976

[54] INHIBITING XANTHINE OXIDASE WITH 3-HALOALKYL SUBSTITUTED BENZOTHIADIAZINE-1,1-DIOXIDES

[75] Inventor: Frederick C. Novello, Berwyn, Pa.

[73] Assignee: Merck & Co., Inc., Rahway, N.J.

[22] Filed: May 24, 1972

[21] Appl. No.: 256,224

[52] U.S. Cl. .............................................. 424/246
[51] Int. Cl. ............................................. A61k 19/02
[58] Field of Search .................................... 424/246

[56] References Cited
UNITED STATES PATENTS

| | | | |
|---|---|---|---|
| 3,137,625 | 6/1964 | Biel ..................................... | 424/246 |
| 3,288,678 | 11/1966 | de Stevens et al. ................. | 424/246 |
| 3,443,004 | 5/1969 | Lachman et al. .................... | 424/246 |
| 3,499,082 | 3/1970 | de Stevens et al. ................. | 424/246 |
| 3,504,089 | 3/1970 | Robison ............................... | 424/246 |

OTHER PUBLICATIONS

Novello et al., Ind. Chim. Belge 1967, 32 (Spec. No.) 222–225.

*Primary Examiner*—Albert T. Meyers
*Assistant Examiner*—Donald B. Moyer
*Attorney, Agent, or Firm*—Daniel T. Szura; J. Jerome Behan

[57] ABSTRACT

Method for decreasing the concentration of uric acid in the blood and urine of a mammal by the administration of a 3-haloalkyl-1,2,4-benzothiadiazine-1,1-dioxide product or 3,4-dihydro derivative thereof. The products employed in this method of treatment are prepared by conventional methods employing the appropriate orthanilamide and haloalkanoic acid halide or carboxaldehyde. The products effect the lowering of the uric acid level by virtue of their xanthine oxidase inhibiting properties.

17 Claims, No Drawings

INHIBITING XANTHINE OXIDASE WITH 3-HALOALKYL SUBSTITUTED BENZOTHIADIAZINE-1,1-DIOXIDES

This invention is concerned with a method of lowering the uric acid level in the blood and urine of a mammal by the administration of a benzothiadiazine compound having a 3-haloalkyl substituent, which products have been found to exhibit xanthine oxidase inhibiting properties comparable to that exhibited by allopurinol when all compounds are evaluated in the same in vitro test.

The products employed in the method of this invention have the structural formula

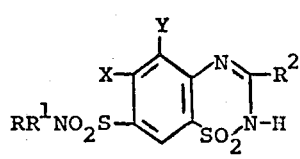

I

OR

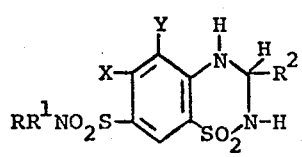

II and pharmacologically acceptable salts thereof wherein R and $R^1$ are similar or dissimilar groups selected from hydrogen and lower alkyl or lower alkenyl having from 1 to 5 carbon atoms, X is selected from halogen and trifluoromethyl, Y is selected from hydrogen, chloro and bromo but particularly hydrogen, and $R^2$ is a mono- or polyhaloalkyl attached through one of its carbon atoms to the benzothiadiazine nucleus, the alkyl moiety advantageously having from 1 to 5 carbon atoms and the halo substituent advantageously being chloro or bromo but also including fluoro and iodo, and when more than one halo substituent is present, they can be the same or different halos.

The active products can be prepared by one or another of the well known procedures for making benzothiadiazine compounds of structure I or 3,4-dihydrobenzothiadiazine compounds of structure II.

In general, the benzothiadiazine compounds of structure I can be prepared by reacting a mixture of the appropriate orthanilamide derivative with the haloalkanoic acid halide which, for practical purposes, can be the acid chloride. The acid chloride can be preformed and employed in the reaction or it can be prepared in situ by the addition of phosphorus oxychloride to a mixture of the orthanilamide and the haloalkanoic acid. When the acid chloride is preformed, the reaction advantageously is conducted in the presence of an inert solvent such as dioxane, tetrahydrofuran, dimethylformamide, and the like and is facilitated by heating up to the reflux temperature of the reaction mixture. When the acid chloride is formed in situ, the phosphorus oxychloride serves not only to form the acid chloride but as solvent as well. Ring closure can be accomplished under acidic or basic conditions.

A conventional method for preparing the 3,4-dihydrobenzothiadiazine of structure II above comprises reacting a mixture of the appropriate orthanilamide derivative with the aldehyde of the selected haloalkanoic acid, generally in the presence of a mineral acid. It is well known that the 3,4-dihydro compounds (II) also can be prepared from the hydro compounds (I) by reduction employing hydrogenation in the presence of ruthenium or by treatment with an alkali metal borohydride or an equivalent reducing agent capable of reducing the double bond. Various methods of reducing the double bond have been described in the literature and any one of these methods can be employed in converting the products of structure I to the products of structure II.

Pharmacologically acceptable salts generally are the alkali metal salts which may be prepared by conventional methods, for example by treatment with an alkali metal hydroxide, e.g. sodium or potassium hydroxide, in a solvent such as a lower alkanol or in water and evaporating the solvent or by reacting the free compound, for example, in an ether, e.g. p-dioxane or diethyleneglycol dimethyl ether solution with an alkali metal hydride or amide and removing the solvent. Mono- or poly-salts may be obtained.

As the active products of the method of this invention are inhibitors of xanthine oxidase, they effectively decrease the concentration of uric acid in the blood and urine of mammals, and additionally increase the excretion of hypoxanthine and xanthine. The method of this invention therefore is particularly useful in the treatment and management of gout preferably by oral administration of from about 100 to 800 mg. per day of the active products in divided doses as prescribed by the physician.

Any of the known methods for formulating thiazide products can be used in the preparation of suitable dosage forms of the 3-haloalkyl derivatives. The following formulation is illustrative of one suitable dosage form:

Compressed Tablet Containing
0.5 g. of Active Ingredient

|  | Grams |
|---|---|
| 3-Chloromethyl-6-chloro-7-N,N-dimethylsulfamoyl-1,2,4-benzothiadiazine-1,1-dioxide | 500.0 |
| Starch paste 12.5%, 100 cc., allow | 12.5 |
|  | 512.5 |
| Starch, U.S.P. corn | 25.0 |
| Magnesium stearate | 5.5 |
|  | 543.0 |

The thiazide is granulated with the starch paste and while moist passed through a No. 14 screen, dried at 45° C. for 20 hours and then passed 3 times through a No. 14 screen. The starch then is passed through a No. 90 bolting cloth onto the granulation and all ingredients are blended thoroughly. Then the magnesium stearate is passed through a No. 90 bolting cloth onto the granulation and these ingredients are blended after which the granulation is compressed into tablets using 14/32 in. flat, bevelled, scored punch having a thickness of 0.205 ± 0.005 in. yielding 1,000 tablets, each weighing 0.543 gram.

The following methods were employed to prepare the products of Structure I.

EXAMPLE 1

3-Chloromethyl-5-bromo-7-sulfamoyl-1,2,4-benzothiadiazine-1,1-dioxide

A mixture of 2,4-disulfamoyl-6-bromoaniline (0.015 mole) and chloroacetyl chloride (0.016 mole) in 50 ml. of dioxane or other inert organic solvent is heated under reflux conditions for about 24 hours and then concentrated to dryness. The residue is dissolved in concentrated sulfuric acid (5 ml. acid/gram), heated in a steam bath at 60°–70° C. for three hours then poured onto ice. The product, 3-chloromethyl-5-bromo-7-sulfamoyl-1,2,4-benzothiadiazine-1,1-dioxide, is purified by recrystallization from a mixture of acetone-alcohol-water.

EXAMPLE 2

3-Chloromethyl-6-bromo-7-sulfamoyl-1,2,4-benzothiadiazine-1,1-dioxide

A mixture of 2,4-disulfamoyl-5-bromoaniline (0.02 mole) and chloroacetyl chloride (0.022 mole) in 75 ml. of dioxane is heated under reflux for about 24 hours and then concentrated to dryness. The residue is dissolved in ethanol and then heated on the steam bath in a mixture of 2.0 g. of potassium or sodium acetate and 50 ml. of water for two hours. The solution is cooled and the product separated by acidification with hydrochloric acid and purified by recrystallization from a mixture of ethanol and water.

The products of Table I were prepared by the procedure of Example 1 or Example 2 as indicated in the table employing the orthanilamide and the haloalkanoic acid halide having the substituents designated in the table. The substituents X, Y, R, $R^1$ and $R^2$ of the starting materials appear unchanged in the end product, I.

TABLE II

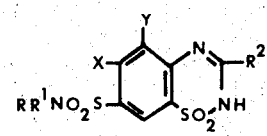

| R | $R^1$ | X | Y | $R^2$ |
|---|---|---|---|---|
| $CH_3$ | H | Cl | H | $-CH_2Cl$ |
| H | H | Cl | H | $-CH_2Cl$ |
| H | H | Cl | H | $-CH_2Br$ |
| H | H | Cl | H | $-CHCl_2$ |
| H | H | Cl | H | $-CCl_3$ |
| H | H | Cl | H | $-CH_2Br$ |
| H | H | Cl | H | $-CHBr_2$ |
| H | H | Cl | H | $-CHBr-CH_3$ |
| H | H | Cl | H | $-CHBr-CH_2CH_3$ |
| H | H | Cl | H | $-CH_2CH_2Cl$ |
| H | H | $CF_3$ | H | $-CH_2CH_2Cl$ |
| H | H | Cl | Cl | $-CH_2Br$ |
| H | H | Br | H | $-CH_2Br$ |
| H | H | F | H | $-CH_2CH_2Cl$ |
| H | H | $CF_3$ | H | $-CH_2F$ |
| H | H | Cl | H | $-CH_2CH_2F$ |
| H | H | $CF_3$ | H | $-CH_2CH_2I$ |
| H | H | Cl | H | $-CHClCH_3$ |
| H | H | $CF_3$ | H | $-CH(CH_3)CH_2Cl$ |
| H | H | Br | H | $-CHClCH_3$ |
| H | H | Cl | H | $-CF_3$ |
| H | H | $CF_3$ | H | $-CH_2Cl$ |
| H | H | $CF_3$ | H | $-CHCl_2$ |
| H | H | $CF_3$ | H | $-CCl_3$ |
| H | H | $CF_3$ | H | $-CH_2Br$ |
| H | H | $CF_3$ | H | $-CHBr_2$ |
| H | H | $CF_3$ | H | $-CHBrCH_3$ |
| H | H | $CF_3$ | H | $-CHBrCH(CH_3)_2$ |
| $CH_3$ | $CH_3$ | $CF_3$ | H | $-CH_2Cl$ |

A general method employed to synthesize the 3,4-dihydrobenzothiadiazine compounds is described in the following example.

TABLE I

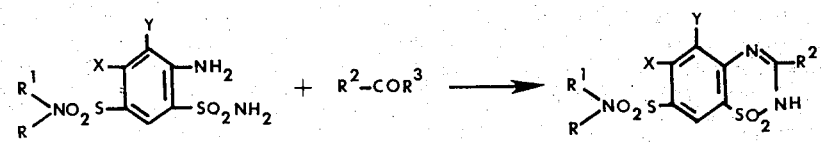

| Ex No. | R | $R^1$ | X | Y | $R^2$ | $R^3$ | Meth of Syn. | m.p. °C. | Formula | Analysis Calculated | | | Found | | |
|---|---|---|---|---|---|---|---|---|---|---|---|---|---|---|---|
| | | | | | | | | | | C | H | N | C | H | N |
| 3 | $CH_3$ | $CH_3$ | Cl | H | $Cl_3C-$ | Cl | 1 | 287–91 | $C_{10}H_9Cl_4N_3O_4S_2$ | 27.23 | 2.06 | 9.53 | 27.47 | 2.22 | 9.46 |
| 4 | $C_2H_5$ | $C_2H_5$ | Cl | H | $Cl_3C-$ | Cl | 1 | 245–48 | $C_{12}H_{13}Cl_4N_3O_4S_2$ | 30.72 | 2.79 | 8.96 | 31.01 | 2.64 | 8.94 |
| 5 | $C_2H_5$ | H | Cl | H | $Cl_2CH-$ | Cl | 1 | 280–84 | $C_{10}H_{10}Cl_3N_3O_4S_2$ | 29.53 | 2.48 | 10.33 | 29.82 | 2.54 | 10.31 |
| 6 | $CH_3$ | $CH_3$ | Cl | H | $Cl_2C(CH_3)-$ | Cl | 1 | 270–74 | $C_{11}H_{12}Cl_3N_3O_4S_2$ | 31.40 | 2.87 | 9.99 | 31.79 | 3.04 | 10.00 |
| 7 | $nC_3H_7$ | $nC_3H_7$ | Cl | H | $BrCH_2-$ | Br | 1 | 232–34 | $C_{14}H_{19}BrClN_3O_4S_2$ | 35.56 | 4.05 | 8.89 | 36.08 | 4.33 | 8.77 |
| 8 | $nC_3H_7$ | $nC_3H_7$ | Cl | Cl | $Cl_3C-$ | Cl | 1 | 168–70 | $C_{14}H_{16}Cl_5N_3O_4S_2$ | 31.62 | 3.03 | 7.90 | 32.18 | 3.04 | 8.28 |
| 9 | $nC_3H_7$ | $nC_3H_7$ | Cl | Cl | $Cl_2CH-$ | Cl | 1 | 220–23 | $C_{14}H_{17}Cl_4N_3O_4S_2$ | 33.81 | 3.45 | 8.45 | 34.35 | 3.48 | 8.48 |
| 10 | $nC_3H_7$ | $nC_3H_7$ | Cl | Cl | $ClCH_2-$ | Cl | 2 | 201–04 | $C_{14}H_{18}Cl_3N_3O_4S_2$ | 36.33 | 3.92 | 9.08 | 36.77 | 4.10 | 8.92 |
| 11 | $nC_3H_7$ | $nC_3H_7$ | Cl | H | $Cl_2CH-$ | Cl | 2 | 215–18 | $C_{14}H_{18}Cl_3N_3O_4S_2$ | 36.33 | 3.92 | 9.08 | 36.63 | 4.14 | 9.07 |
| 12 | $CH_3$ | $CH_3$ | $CH_2Br-$ | | Cl | 2 | 270–73 | $C_{10}H_{11}Cl_2N_3O_4S_2$ | 32.26 | 2.98 | 11.29 | 32.61 | 2.97 | 11.24 |
| 13 | $nC_3H_7$ | $nC_3H_7$ | Cl | H | $ClCH_2-$ | Cl | 2 | 249–52 | $C_{14}H_{19}Cl_2N_3O_4S_2$ | 39.25 | 4.47 | 9.81 | 39.49 | 4.47 | 9.71 |
| 14 | $nC_3H_7$ | $nC_3H_7$ | Cl | H | $Cl_3C-$ | Cl | 2 | 218–21 | $C_{14}H_{17}Cl_4N_3O_4S_2$ | 33.82 | 3.45 | 8.45 | 34.28 | 3.82 | 8.41 |
| 15 | $CH_3$ | $CH_3$ | Cl | H | $Cl_2CH-$ | Cl | 1 | 269–72 | $C_{10}H_{10}Cl_3N_3O_4S_2$ | 29.53 | 2.48 | 10.33 | 29.71 | 2.69 | 10.33 |
| 16 | $C_2H_5$ | $C_2H_5$ | Cl | H | $Cl_2CH-$ | Cl | 2 | 241–43 | $C_{12}H_{14}Cl_3N_3O_4S_2$ | 33.15 | 3.24 | 9.66 | 33.44 | 3.18 | 9.58 |
| 17 | $C_2H_5$ | $C_2H_5$ | Cl | H | $ClCH_2-$ | Cl | 2 | 234–35 | $C_{12}H_{15}Cl_2N_3O_4S_2$ | 36.25 | 3.77 | 10.50 | 36.08 | 3.61 | 10.34 |
| 18 | $CH_2=CHCH_2$ | $CH_2=CHCH_2$ | Cl | H | $ClCH_2-$ | Cl | 2 | 187–90 | $C_{14}H_{15}Cl_2N_3O_4S_2$ | 39.63 | 3.56 | 9.90 | 38.82 | 3.68 | 9.84 |

Additional known 3-haloalkyl products having structure I that can be used in the method of this invention are identified in Table II.

EXAMPLE 19

3-Trichloromethyl-6-chloro-7-N,N-di-n-propylsulfamoyl-3,4-dihydro-1,2,4-benzothiadiazine-1,1-dioxide A solution of 2-sulfamoyl-4-N,N-di-n-propylsulfamoyl-5-chloroaniline (0.01 mole) and trichloroacetaldehyde (0.011 mole) in 60 ml. of water, 2 ml. of ethanol and 1.5 ml. of concentrated hydrochloric acid is heated under reflux for two hours. The hot mixture is filtered and the product purified by recrystallization from a mixture of dimethylformamide and water providing product melting at 226.5°–228° C.

Analysis calculated for $C_{14}H_{19}Cl_4N_3O_4S_2$: C, 25.19; H, 2.11; N, 9.79; Found: C, 25.44; H, 2.31; N, 9.92.

The substituents attached to the orthanilamide and aldehyde reactants as well as the end product, structure II, are identified in Table II along with the melting point and analysis for the end product obtained by the method of synthesis described in Example 19.

procedure designed to evaluate xanthine oxidase inhibiting properties of compounds. The procedure used employed the principals described in J. Pharm. Sci. 56:955 (1967), Baker et al, and was carried out in the following manner:

A reference cuvette is filled with 0.05M pH 7.4 buffer. For the control, mix quickly in a cuvette 2 ml. hypoxanthine solution ($6 \times 10^{-5}$M), 2 ml. 0.05M pH 7.4 buffer solution, and 2 ml. xanthine oxidase solution, and immediately record the absorbance at 292 $\mu$ for one minute. For the test solution, add quickly to a separate cuvette 2 ml. hypoxanthine solution ($6 \times 10^{-5}$M), 2 ml. test solution, and 2 ml. xanthine oxidase solution, and immediately record the absorbance at 292 $\mu$ for 1 minute. If the inhibition is less than 100%, the % inhibition is calculated as follows:

$$\frac{\Delta A \text{ control} - \Delta A \text{ test}}{\Delta A \text{ control}} \times 100$$

TABLE III

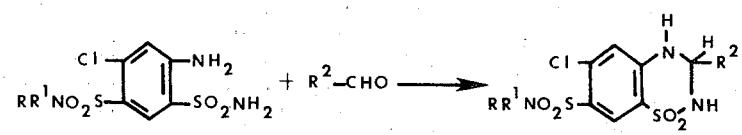

| Ex No. | R | R¹ | R² | m.p. °C. | Formula | ANALYSIS Calculated | | | Found | | |
|---|---|---|---|---|---|---|---|---|---|---|---|
| | | | | | | C | H | N | C | H | N |
| 20 | CH₃ | CH₃ | —CH₂Cl | 208–10 | $C_{10}H_{13}Cl_2N_3O_4S_2$ | 32.09 | 3.50 | 11.23 | 32.38 | 3.37 | 11.21 |
| 21 | CH₂=CHCH₂— | CH₂=CHCH₂— | —CCl₃ | 207–09 | $C_{14}H_{15}Cl_4N_3O_4S_2$ | 33.95 | 3.05 | 8.49 | 34.46 | 2.96 | 8.50 |
| 22 | C₂H₅ | H | —CCl₃ | 269–71 | $C_{10}H_{11}Cl_4N_3O_4S_2$ | 27.10 | 2.50 | 9.48 | 27.43 | 2.53 | 9.34 |
| 23 | CH₃ | CH₃ | —CHCl₂ | 238–40 | $C_{10}H_{12}Cl_3N_3O_4S_2$ | 29.39 | 2.96 | 10.28 | 29.48 | 3.33 | 10.38 |
| 24 | CH₃ | H | —CCl₃ | 279–84 | $C_9H_9Cl_4N_3O_4S_2$ | 25.19 | 2.11 | 9.79 | 25.44 | 2.31 | 9.92 |

Additional known 3-haloalkyl products having structure II that can be used in the method of this invention are identified in Table IV.

TABLE IV

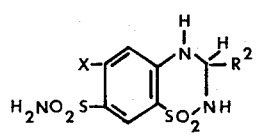

| X | R² |
|---|---|
| Cl | —CCl₃ |
| Cl | —CHCl₂ |
| Cl | —CF₂CF₃ |
| Cl | —CH₂Cl |
| Cl | —CH₂Br |
| Cl | —CH₂I |
| Cl | —CHBrCH₃ |
| Cl | —CHBrCH(CH₃)₂ |
| Cl | —CBr(CH₃)C₂H₅ |
| Br | —CHCl₂ |
| F | —CHCl₂ |
| CF₃ | —CHCl₂ |
| Cl | —CHClBr |
| Cl | —CHBr₂ |
| Cl | —CHF₂ |
| Cl | —CCl₂CH₃ |
| Cl | —CF₂CH₂Cl |
| Cl | —CF₃ |

Representative 3-haloalkylbenzothiadiazines were found to be effective when tested by an art recognized where $\Delta A$ is the change in absorbance in 1 minute. If the inhibition is 100%, the test solution is serially diluted to determine the concentration required for 50% inhibition.

The percent inhibition effected by certain representative products employed in the method of this invention is provided in the following table. The concentration of the test compound was $2 \times 10^{-5}$M unless otherwise noted. For comparison $3.2 \times 10^{-6}$M of allopurinol, a known xanthine oxidase inhibiting agent, effects 50% inhibition of xanthine oxidase by this protocol.

TABLE V

Structure I Compounds:

| R | R¹ | X | Y | R² | % Inhibition |
|---|---|---|---|---|---|
| n-C₃H₇ | n-C₃H₇ | Cl | H | CHCl₂ | 12 |
| CH₃ | CH₃ | Cl | H | CH₂Cl | 52 |
| n-C₃H₇ | n-C₃H₇ | Cl | H | CH₂Cl | 69 |
| n-C₃H₇ | n-C₃H₇ | Cl | H | CCl₃ | 14 |
| CH₃ | CH₃ | Cl | H | CHCl₂ | 11 |
| C₂H₅ | C₂H₅ | Cl | H | CHCl₂ | 18 |
| C₂H₅ | C₂H₅ | Cl | H | CH₂Cl | 75 |
| CH₂=CHCH₂ | CH₂=CHCH₂ | Cl | H | CH₂Cl | 53 |
| CH₃ | CH₃ | Cl | H | CCl₃ | 5 |
| C₂H₅ | C₂H₅ | Cl | H | CCl₃ | 3 |
| C₂H₅ | H | Cl | H | CHCl₂ | 6 |
| H | H | Cl | H | CH₂Cl | 24 |
| CH₃ | CH₃ | Cl | H | CCl₂CH₃ | 13 |
| CH₃ | H | Cl | H | CH₂Cl | 78 |
| n-C₃H₇ | n-C₃H₇ | Cl | H | CH₂Br | 30 |
| n-C₃H₇ | n-C₃H₇ | Cl | Cl | CCl₃ | 26 |
| n-C₃H₇ | n-C₃H₇ | Cl | Cl | CHCl₂ | 21 |
| n-C₃H₇ | n-C₃H₇ | Cl | Cl | CH₂Cl | 33 |

Structure II Compounds
| n-C₃H₇ | n-C₃H₇ | Cl | H | CCl₃ | 6 |

TABLE V-continued

| | | | | | |
|---|---|---|---|---|---|
| $CH_2=CHCH_2$ | $CH_2=CHCH_2$ | Cl | H | $CCl_3$ | 6 |
| $C_2H_5$ | H | Cl | H | $CCl_3$ | 63 |
| $CH_3$ | H | Cl | H | $CCl_3$ | 16 |
| H | H | Cl | H | $CCl_3$ | 45 |

① % Inhibition at $2 \times 10^{-6}$

I claim:

1. A method for inhibiting the action of xanthine oxidase in a mammal having an elevated blood uric acid level by orally administering to said mammal a dose sufficient to lower the blood uric acid level to normal for that species of a xanthine oxidase inhibitor selected from the group consisting of structure I and structure II:

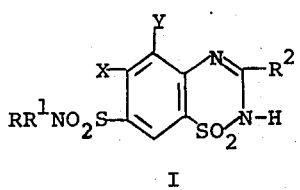

I

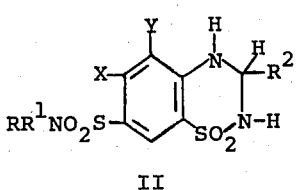

II or sodium or potassium salt thereof wherein R represents hydrogen, $C_{1-3}$ alkyl or allyl; $R^1$ represents hydrogen, $C_{1-3}$ alkyl or allyl; X represents halogen or trifluoromethyl; Y represents hydrogen, chloro or bromo; and $R^2$ represents mono- or polyhalo $C_{1-5}$ alkyl.

2. The method of claim 1 wherein an active product having structure I is employed.

3. The method of claim 2 wherein in the product of structure I R and $R^1$ are each $C_{1-3}$ alkyl.

4. The method of claim 2 wherein the product of structure I R and $R^1$ each represent $C_{1-3}$ alkyl, X is chloro and Y is hydrogen.

5. The method of claim 2 wherein in the product of structure I R and $R^1$ each represent $C_{1-3}$ alkyl, X is chloro, Y is hydrogen and $R^2$ is chloromethyl.

6. The method of claim 2 wherein the active product is 3-chloromethyl-6-chloro-7-dimethylsulfamoyl-1,2,4-benzothiadiazine-1,1-dioxide.

7. The method of claim 2 wherein in the product of structure I X is trifluoromethyl and Y is hydrogen.

8. The method of claim 2 wherein in the product of structure I R and $R^1$ each represent $C_{1-3}$ alkyl, X is trifluoromethyl, Y is hydrogen and $R^2$ is chloromethyl.

9. The method of claim 2 wherein the active product is 3-chloromethyl-6-trifluoromethyl-7-dimethylsulfamoyl-1,2,4-benzothiadiazine-1,1-dioxide.

10. The method of claim 2 wherein the active product is 3-chloromethyl-6-trifluoromethyl-7-sulfamoyl-1,2,4-benzothiadiazine-1,1-dioxide.

11. The method of claim 1 wherein an active product having structure II is employed.

12. The method of claim 11 wherein in the product having structure II, X is chloro and Y is hydrogen.

13. The method of claim 11 wherein in the product having structure II, X is chloro, Y is hydrogen, R is $C_{1-3}$ alkyl and $R^1$ is hydrogen.

14. The method of claim 11 wherein the active product is 3-trichloromethyl-6-chloro-7-ethylsulfamoyl-3,4-dihydro-1,2,4-benzothiadiazine-1,1-dioxide.

15. The method of claim 11 wherein in the product of structure II, X is trifluoromethyl and Y is hydrogen.

16. The method of claim 11 wherein the active product is 3-chloromethyl-6-trifluoromethyl-7-sulfamoyl-3,4-dihydro-1,2,4-benzothiadiazine-1,1-dioxide.

17. The method of claim 1 wherein from about 100 to 800 milligrams per day of the xanthine oxidase inhibitor is administered in divided doses.

* * * * *